United States Patent
Waits

(10) Patent No.: US 11,869,642 B2
(45) Date of Patent: *Jan. 9, 2024

(54) SYSTEM AND METHOD TO FACILITATE INTEROPERABILITY OF HEALTH CARE MODULES

(71) Applicant: KicStand, Inc., Houston, TX (US)

(72) Inventor: Daniel W. Waits, San Diego, CA (US)

(73) Assignee: KICSTAND, INC., Houston, TX (US)

( * ) Notice: Subject to any disclaimer, the term of this patent is extended or adjusted under 35 U.S.C. 154(b) by 59 days.

This patent is subject to a terminal disclaimer.

(21) Appl. No.: 17/467,592

(22) Filed: Sep. 7, 2021

(65) Prior Publication Data
US 2021/0398628 A1    Dec. 23, 2021

Related U.S. Application Data

(63) Continuation of application No. 17/084,973, filed on Oct. 30, 2020, which is a continuation of application No. 15/715,359, filed on Sep. 26, 2017, now Pat. No. 10,861,589.

(51) Int. Cl.
*G16H 10/60* (2018.01)
*G16H 40/20* (2018.01)
*G16H 20/10* (2018.01)

(52) U.S. Cl.
CPC ............. *G16H 10/60* (2018.01); *G16H 20/10* (2018.01); *G16H 40/20* (2018.01)

(58) Field of Classification Search
CPC ................................ G16H 10/60; G16H 20/10
See application file for complete search history.

(56) References Cited

U.S. PATENT DOCUMENTS

| | | | |
|---|---|---|---|
| 6,345,259 B1 | 2/2002 | Sandoval | |
| 8,019,621 B2 | 9/2011 | Zhu et al. | |
| 8,595,206 B1 | 11/2013 | Ansari et al. | |
| 10,311,536 B1 | 6/2019 | Ansari et al. | |
| 10,347,374 B2 | 7/2019 | Tribble et al. | |
| 10,417,387 B2 | 9/2019 | Toupin et al. | |
| 2006/0277076 A1 | 12/2006 | Hasan et al. | |
| 2010/0324936 A1* | 12/2010 | Vishnubhatla | G06Q 40/08 715/810 |
| 2011/0066260 A1 | 3/2011 | Condurso et al. | |
| 2011/0313790 A1 | 12/2011 | Yao | |
| 2012/0078664 A1* | 3/2012 | Hasan | G16H 10/60 705/3 |

(Continued)

*Primary Examiner* — Jay M. Patel
(74) *Attorney, Agent, or Firm* — BAKER BOTTS L.L.P.

(57) ABSTRACT

A system for facilitating interoperability among health care modules includes an interface configured to receive a first electronic record from a first health care module. The first electronic record has a first data structure. The system also includes a processor communicatively coupled to the interface. The processor is configured to analyze the first electronic record having the first data structure, and, based on the analysis, extract a portion of data from the first electronic record. The processor further creates a second electronic record using the portion of data from the first electronic record, where the second electronic record has a second data structure. The second data structure is configured to be compatible with a second health care module. The interface is further configured to transmit the second electronic record for display to the second health care module.

20 Claims, 8 Drawing Sheets

(56) References Cited

U.S. PATENT DOCUMENTS

| | | |
|---|---|---|
| 2013/0110547 A1 | 5/2013 | Englund et al. |
| 2013/0124482 A1 | 5/2013 | Atamna et al. |
| 2013/0218589 A1 | 8/2013 | Lerner |
| 2014/0244296 A1* | 8/2014 | Linn .................... G16H 40/20 705/3 |
| 2014/0279269 A1 | 9/2014 | Brantley et al. |
| 2015/0161351 A1 | 6/2015 | Scalpati |
| 2015/0294084 A1 | 10/2015 | McCauley et al. |
| 2015/0310176 A1 | 10/2015 | Chen et al. |
| 2016/0103963 A1 | 4/2016 | Mishra |
| 2017/0344716 A1 | 11/2017 | Abou-Sayed et al. |

* cited by examiner

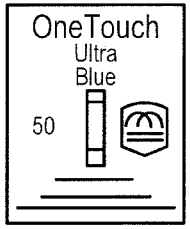

OneTouch Ultra Glucose Strips (50) count

| | |
|---|---|
| Prescription ID: | 187 |
| Status: | New prescription on file |
| Pick up at: | SOME, INC. |
| Prescribed by: | Health Care, MD |
| HCP Taxonomy: | Urology |
| Alternative prescription: | Accuchek Aviva Glucose Strips (50) |
| Created: | Jul 18, 2017 |

Prescription details

| | |
|---|---|
| Dosage & directions: | Test 5-10 times per day |
| Expire date: | 30 days |
| Drug strength: | n/a |
| Purpose: | Diabetes |
| Quantity: | 300 |

✓ Branded products only

Insurance information

| | |
|---|---|
| Insurance: | Cigna |
| Covered: | Yes |
| Copay: | $0 |
| Deductible: | Met |
| Insurance ID: | 123 |
| Insurance group: | 123 |
| Insurance BIN: | 123 |
| Insurance PCN: | ABC |
| Payment type: | Durable Medical Equipment |

You can start a chat with a fulfillment center and health care professional to discuss current prescription. Start a conversation:

*FIG. 5C*

Create a new prescription

Patient

👤 Example Example   X

Prescriptions

Add new prescription

⊘ Lovastatin 20mg   X

Prescription details

Prescription name:
Lovastatin 20mg

☑ Choose fulfillment company from the list

Choose fulfillment company   ▽

Alternative:   Atorvastatin 20mg ✓
            *Use this product*

Dosage & directions

Duration   ▽

Drug strength

Purpose*   ▽

Quantity (pills)

☑ Branded products only

Cancel   [ Send ]

| Insurance information | ⊘ |
|---|---|
| Insurance: | Cigna |
| Covered: | No |
| Copay: | $0 |
| Insurance ID: | 123 |
| Insurance group: | 123 |
| Insurance BIN: | 123 |
| Insurance PCN: | ABC |
| Contact phone: | 555-555-5555 |
| Pharmacy help phone: | 555-555-5555 |
| Precertification phone: | 555-555-5555 |

*FIG. 6*

SYSTEM AND METHOD TO FACILITATE INTEROPERABILITY OF HEALTH CARE MODULES

PRIORITY

This application is a continuation, under 35 U.S.C. § 120, of U.S. patent application Ser. No. 17/084,973 filed on Oct. 30, 2020 which is a continuation, under 35 U.S.C. § 120 of U.S. patent application Ser. No. 15/715,359 filed on Sep. 26, 2017 and entitled "System And Method To Facilitate Interoperability Of Health Care Modules" incorporated herein by reference.

TECHNICAL FIELD

The present disclosure relates generally to health care modules and, more specifically, to a system and method to facilitate interoperability of health care modules.

BACKGROUND

Health care organizations typically comprise their own computer systems, modules, and electronic records for storing information about patients, health care professionals, pharmacies, and insurance companies. The records may be incompatible such that the information within the records cannot be easily shared or understood by separate health care organizations and modules. Current practices for communicating and sharing electronic records in the health care industry are limited.

SUMMARY OF EXAMPLE EMBODIMENTS

According to embodiments of the present disclosure, disadvantages associated with incompatibility among various health care modules may be reduced or eliminated.

In accordance with a particular embodiment of the present disclosure, a system for facilitating interoperability among health care modules includes an interface configured to receive a first electronic record from a first health care module. The first electronic record has a first data structure. The system also includes a processor communicatively coupled to the interface. The processor is configured to analyze the first electronic record having the first data structure, and, based on the analysis, extract a portion of data from the first electronic record. The processor further creates a second electronic record using the portion of data from the first electronic record, where the second electronic record has a second data structure. The second data structure is configured to be compatible with a second health care module. The interface is further configured to transmit the second electronic record for display to the second health care module.

In accordance with another aspect of the present disclosure, a method for facilitating interoperability among health care modules includes receiving, by an interface, a first electronic record from a first health care module, where the first electronic record having a first data structure. The method also includes analyzing, by a processor, the first electronic record having the first data structure, and based on the analysis, extracting, by the processor, a portion of data from the first electronic record. The method further includes, creating, by the processor, a second electronic record using the portion of data from the first electronic record, the second electronic record having a second data structure, wherein the second data structure is configured to be compatible with a second health care module. The method finally includes transmitting, by the interface, the second electronic record for display to the second health care module.

In accordance with another aspect of the present disclosure, a non-transitory computer-readable medium encoded with logic, the logic, when executed by a processor, is operable to receive a first electronic record from a first health care module, where the first electronic record having a first data structure. The logic is further operable to analyze the first electronic record having the first data structure, and based on the analysis, extract a portion of data from the first electronic record. The logic is further operable to create a second electronic record using the portion of data from the first electronic record, where the second electronic record having a second data structure. The second data structure is configured to be compatible with a second health care module. Finally, the logic is operable to transmit the second electronic record for display to the second health care module.

Technical advantages of particular embodiments of the present disclosure include reconfiguring an existing data structure to create a new data structure to allow health care modules to communicate health care information between disparate components. This improvement alleviates compatibility concerns between different systems components, thereby creating increased flexibility in exchanging electronic records. Additionally, a system may be configured to analyze data in an electronic record and extract a portion of data from the electronic record, thereby conserving the computational resources and bandwidth consumed by unnecessarily extracting all of the data, some of which may be irrelevant.

In an embodiment, a system is configured to create a first user profile and associate the first user profile with other user profiles, thereby conserving the computational resources and bandwidth consumed by adding additional information contained in other user profiles to the first user profile.

In an embodiment, a system is configured to create a second electronic record that is compatible with more than one health care module, thereby conserving the computational resources and bandwidth consumed by creating and maintaining duplicate electronic records, each in a different format unique to each health care module.

Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present disclosure and for further features and advantages thereof, reference is now made to the following description taken in conjunction with the accompanying drawings, in which:

FIGS. 5A-C illustrate example user profiles that may facilitate interoperability among health care modules; and FIG. 6 illustrates an example interface for creating a new prescription and facilitating interoperability between health care professional modules, patient modules, and pharmacy modules.

DETAILED DESCRIPTION

Figure 1:
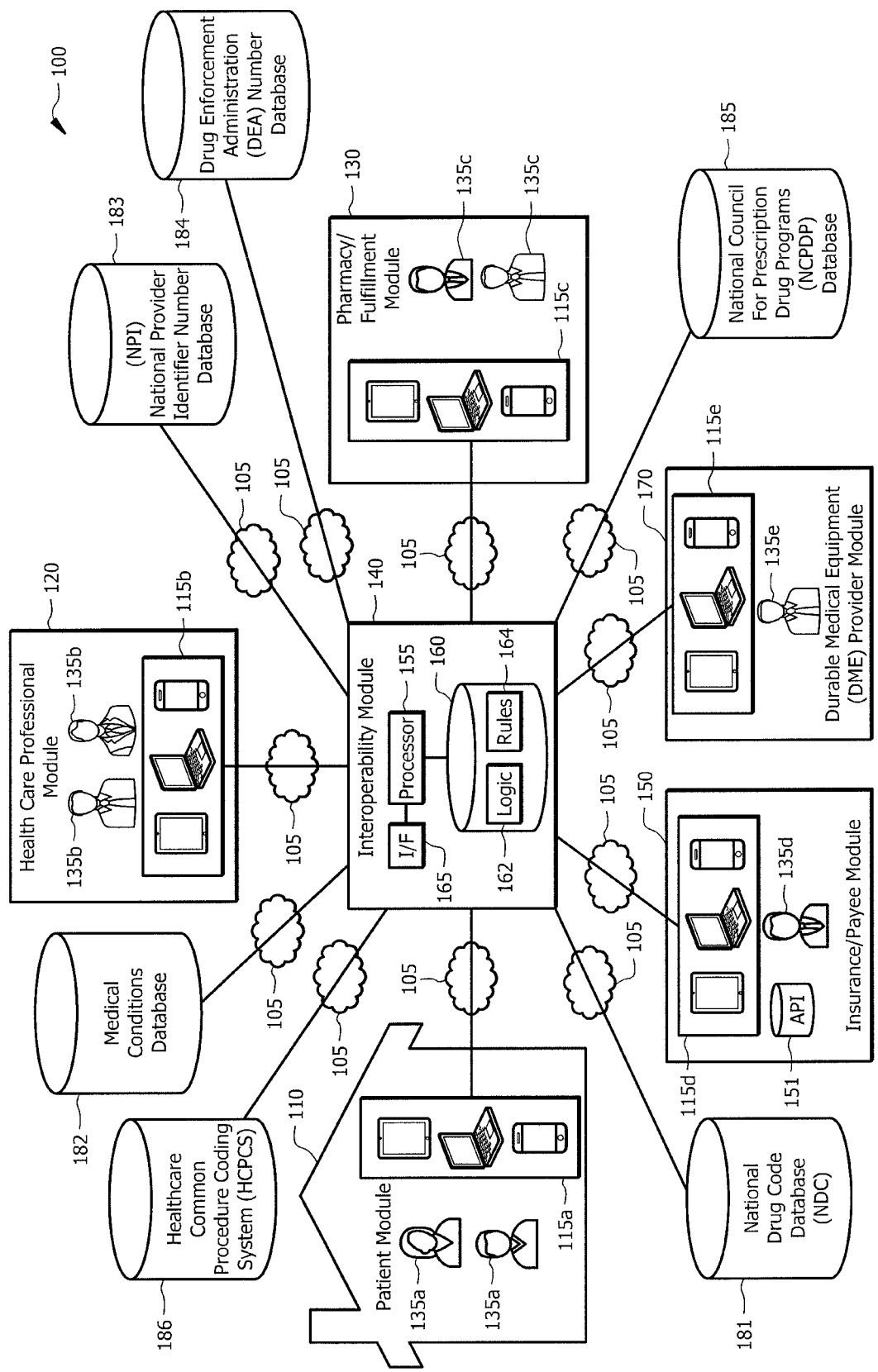
FIG. 1 illustrates an example system that facilitates interoperability of health care modules.

Embodiments of the present disclosure and its advantages are best understood by referring to FIGS. 1-6, like numerals being used for like and corresponding parts of the various drawings.

Current practices in the health care industry include various ways of storing, maintaining, accessing, and analyzing electronic documents, such as medical records, insurance information, prescription information, and any other information or document used by those in the health care industry. For example, health care professionals, pharmacies, insurance companies, and others may each have separate modules, systems, data, and records, that are maintained in different ways such that electronic information cannot be easily shared among them. By having such disparate record-keeping and information-storing practices, it makes coordination among the modules in the health care industry difficult, time consuming, and inefficient. For example, if a patient goes to see four different health care professionals, each health care professional may maintain its own electronic health records using a specific program and/or specific format. These electronic health records cannot be shared among the four health care professionals because one format of a health record at one health care professional's office would not be recognized or understood by another system such that the data may be incorporated into each unique system. Further, the information cannot be easily shared such that each health care professional receives up-to-date patient information, and can coordinate on the patient's health. Instead, a patient must fill out new, updated health forms during each visit to the health care professional's office, which must then be entered into its own electronic health record system, thus expending additional computational resources as well as employee time.

As another example, a pharmacy or fulfillment center may have a completely different system and electronic health records than an insurance company or payee. When a pharmacy employee needs to fulfill a prescription by a health care professional for a patient, it cannot send any electronic information to the insurance company due to the different systems and modules at each. If a pharmacy employee attempted to transmit electronic prescription information to the insurance company, the insurance company's system would not be able to accurately access the information needed to determine whether a prescription is covered. Instead, a pharmacy employee must manually contact the insurance company (e.g., by phone) and have an employee of the insurance company enter the relevant information, determine whether a prescription is covered, and then provide the coverage information to the pharmacy employee. It is an inefficient system that requires duplication in electronic medical, health, and pharmaceutical records. Certain databases commonly used in the health care industry to provide information about health care professionals, medical conditions, or drug information may similarly maintain data in particular formats such that accessing information from any of them may require a unique module and/or data processing system.

Thus, it may be desirable to have a system that facilitates interoperability among the various organizations, medical professionals, systems, and electronic data formats used in the health care industry. The teachings of this disclosure recognize that the use of different systems and formats for electronic records may prevent those in the medical industry from sharing electronic records regarding health information. By facilitating interoperability among health care modules, electronic records in various formats and health information may be efficiently and accurately shared, thus conserving computational resources and bandwidth consumed by unnecessarily maintaining duplicate copies of the same data in different formats at each of the various systems.

FIG. 1 illustrates an example system 100 that facilitates interoperability of health care modules and databases. System 100 may include interoperability module 140, patient module 110, health care professional module 120, pharmacy/fulfillment module 130, insurance/payee module 150, medical conditions database 182, National Provider Identifier (NPI) number database 183, Drug Enforcement Administration (DEA) number database 184, National Council for Prescription Drug Programs (NCPDP) database 185, National Drug Code (NDC) database 181, and Durable Medical Equipment (DME) provider module 170. System 100 may be connected by network 105.

In general, interoperability module 140 receives a first electronic record from a first health care module, the first electronic record having a first data structure. Interoperability module 140 may further analyze the first electronic record having the first data structure, and, based on the analysis, extract a portion of data from the first electronic record. Interoperability module 140 may also create a second electronic record using the portion of data from the first electronic record, the second electronic record having a second data structure. The second data structure may be configured to be compatible with a second health care module. Finally, interoperability module 140 may be further configured to transmit the second electronic record for display to the second health care module.

Network 105 may refer to any interconnecting system capable of transmitting audio, video, signals, data, messages, or any combination of the preceding. Network 105 may include all or a portion of a public switched telephone network (PSTN), a public or private data network, a local area network (LAN), a metropolitan area network (MAN), a wide area network (WAN), a local, regional, or global communication or computer network such as the Internet, a wireline or wireless network, an enterprise intranet, a cellular network, or any other suitable communication link, including combinations thereof.

Network 105 may communicatively couple the various modules (e.g., patient module 110, health care professional module 120, fulfillment modules (i.e., pharmacy module 130 and DME provider module 170), and/or insurance module 150) and databases (e.g., medical conditions database 182, NPI number database 183, DEA number database 184, NCPDP database 185, HCPCS database 186, and/or NDC database 181) of system 100 to interoperability module 140.

In some embodiments, system 100 comprises a number of modules that service different entities and/or organizations in the health care industry. These modules may include patient module 110, health care professional module 120, pharmacy module 130, insurance module 150, and DME provider module 170.

Modules 110, 120, 130, 150, and 170 may be any suitable combination of hardware and/or software implemented in one or more modules to process data. In some embodiments, each module may be accessed by users 135a-d utilizing user devices 115a-d. Each module may store electronic records, such as patient health records, insurance information (e.g., prescription coverage and deductibles), medication and fulfillment information, or any other records relating to health care. For example, health care professional module 120 may track patient information, health care records, and appointment schedules. As another example, insurance module 150 may track patient information, prescription information, and deductible information. In some embodiments, patient module 110 may need access to an electronic record from health care professional module 120 (e.g., prescription information). Interoperability module 140, in some embodiments, may facilitate patient module 110 accessing electronic records from health care professional module 120. Interoperability module 140 may receive a request from patient module 110 regarding electronic records, determine the necessary records, and extract the necessary portion of data from the necessary electronic records. For example, patient module 110 may request certain information about a prescription, such as dosage instructions, and interoperability module 140 may access all the prescription information from health care professional module 120, extract the dosage instructions, and provide that information to patient module.

User devices 115a-d may refer to any device that allows users 135a-d to communicate with and receive information from other modules in system 100 through interoperability module 140. In some embodiments, user devices 115a-d may include a computer, workstation, telephone, Internet browser, electronic notebook, Personal Digital Assistant (PDA), pager, or any other suitable device (wireless, wireline, or otherwise), component, or element capable of receiving, processing, storing, and/or communicating information with other components of system 100. User devices 115a-d may also comprise any suitable user interface such as a display, microphone, keyboard, electronic pen, or any other appropriate terminal equipment usable by user 135a-d. It will be understood that system 100 may comprise any number and combination of user devices 115a-d. Users 135a-d utilize user devices 115a-d to interact with interoperability module 140 and other modules of system 100, as described below. In some embodiments, users 135a-d may be a patient, caregiver, heath care professional, pharmacists, technician, insurance administrator, or any other person needing to access a component of system 100.

Patient module 110 may be any suitable combination of hardware and/or software implemented in one or more modules to process data for user 135a, such as a patient or caregiver for a patient. Patient module 110 may store and process data related to patient 135a, such as medical records, prescription information (i.e., for medications, drugs, medical equipment and devices, and/or any other wellness benefit), medical conditions, preferred pharmacies, or any other information related to the health of patient 135. In some embodiments, user 135 may be a caregiver that provides care to a patient. Examples of caregivers 135a may be a parent of a child patient, a family member, an in-home nurse or technician for a sick and/or elderly patient, a nursing home attendant, or anyone tasked with providing care to patient 135a. In some embodiments, caregivers 135a may be able to access patient module 110 for one or more patients 135a to which caregiver 135a is providing care. In some embodiments, system 100 does not include patient module 110, and patient 135a may store all of the health records of the patient in interoperability module 140. Patient 135a may utilize user device 115a through network 105 to input and receive information from interoperability module 140 and other components of system 100. In some embodiments, interoperability module 140 facilitates patient module 110 operating in conjunction with other modules, such as health care professional module 120, pharmacy module 130, DME provider module 170, and/or insurance module 150.

Health care professional module 120 may be any suitable combination of hardware and/or software implemented in one or more modules to process data for user 135b, such as a doctor, nurse practitioner, physician's assistant, technician, administrative assistant, or any other employee working with a health care professional. Health care professional module 120 may store and process data related to health care professional 135b (e.g., NPI number, DEA number, taxonomy, specialties, address, and/or phone number), health care information, and records of one or more patients 135a, or any other information related to health care professional 135b. In some embodiments, health care professional module 120 is associated with a physical location, such as a hospital or doctor's office. In some embodiments, system 100 does not include health care professional module 120, and health care professional 135b may store all of the records in interoperability module 140. Health care professional 135b may utilize user device 115b through network 105 to input and receive information from interoperability module 140 and other components of system 100. In some embodiments, interoperability module 140 facilitates health care professional module 120 operating with other modules, such as patient module 110, pharmacy module 130, DME provider module 170, and/or insurance module 150.

Pharmacy module 130 may be any suitable combination of hardware and/or software implemented in one or more modules to process data for user 135c, such as a pharmacist, a technician, a pharmacy employee, or any other employee working with pharmacist 135c. In some embodiments, pharmacy module 130 may be associated with a pharmacy organization or brand, and/or a physical pharmacy store location. Pharmacy module 130 may store and process data related to pharmacist 135c (name, NPI number, accreditation and/or schooling), a pharmacy company (name, related insurance companies, locations of stores, NPI number), or a physical store of the pharmacy company (address, store hours, NPI number). Pharmacy module 130 may further store and process data relating to prescriptions and prescription fulfillment (e.g., for one or more patients 135a), as well as insurance and deductible information. In some embodiments, system 100 does not include pharmacy module 130, and pharmacist 135c or the pharmacy itself may store all of the records in interoperability module 140. Pharmacist 135c may utilize user device 115c through network 105 to input and receive information from interoperability module 140 and other components of system 100. In some embodiments, interoperability module 140 facilitates pharmacy module 130 operating with other modules, such as patient module 110, health care professional module 120, and/or insurance module 130. Interoperability module 140 may access information from other modules that is inaccessible to pharmacy module 130. For example, interoperability module 140 may access insurance information of patient 135a from insurance module 130 and provide the required portion of data from the insurance records to pharmacy module 130, such that a prescription may be filled.

Insurance module 150 may be any suitable combination of hardware and/or software implemented in one or more modules to process data for user 135d, such as an insurance agent or other insurance employee. In some embodiments, insurance module 150 may be associated with an insurance company and/or a physical location of an insurance center. Insurance module 150 may store and process data related to patient 135 (e.g., name, address, prescription information, insurance information, medical coverage, deductible information). In some embodiments, insurance module 150 comprises application program interface (API) database 151 that stores insurance information. API database 151 may refer to any suitable device capable of storing and facilitating retrieval of insurance data. API database 151 may store electronic records regarding insurance information, such as information about patient 135*a*, type of insurance, payment requirements, prescription coverage, or any other information related to insurance. API database 151 facilitates determining and processing insurance claims, and provides information such as coverage, deductible, copayment, and any other information related to insurance. In some embodiments, interoperability module 140 may access API database 151 in order to provide up-to-date coverage information to users 135, such as patient 135*a*, health care professional 135*b*, and/or pharmacist 135*c*. In some embodiments, system 100 does not include insurance module 150, and insurance agent 135*d* or the insurance company itself may store all of the records in interoperability module 140. Insurance agent 135*d* may utilize user device 115*d* through network 105 to input and receive information from interoperability module 140 and other components of system 100. In some embodiments, interoperability module 140 facilitates insurance module 150 operating with other modules, such as patient module 110, health care professional module 120, DME provider module 170, and/or pharmacy module 130. Interoperability module 140 may access electronic records of insurance information that may be inaccessible to other modules. Interoperability module 140 may extract portions of electronic records of insurance information to facilitate the operation of other modules. For example, interoperability module 140 may extract a portion of data related to coverage of a prescription drug and deliver that portion of data to pharmacy module 130, such that pharmacy module 130 may fulfill the prescription and charge patient 135*a* accordingly.

In some embodiments, DME provider module 170 may be any suitable combination of hardware and/or software implemented in one or more modules to process data regarding medical equipment for patient 135*a* by employee 135*e*. DME provider module 170 may store and process data related to patient 135*a* (e.g., name, insurance information, medical equipment needed, medical conditions) in order to provide proper medical equipment. DME provider module 170 may be associated with a DME provider, which may refer to an organization and/or physical location or store that provides, sells, houses, or develops medical equipment. Patient 135*a* may visit the DME provider in order to purchase or receive certain medical equipment. For example, if patient 135*a* has diabetes, patient 135*a* may visit a pharmacy to receive insulin, blood glucose strips, and other necessities, but must to go DME provider to receive an insulin pump. In some embodiments, DME provider module 170 may be used to create a profile for one or more DME providers. For example, the profile may indicate the medical equipment provided, manufacturer, name, address, or any other information associated with the DME provider. In some embodiments, interoperability module 170 may facilitate associating a DME provider (e.g., DME provider profile) with other users 135. For example, if patient 135*a* receives an insulin pump from DME provider, patient 135*a* may associate its profile with the profile of the DME provider. In this manner, patient 135*a* may have DME provider's information readily available, for example, if patient 135*a* needs the address to pick up medical equipment. In some embodiments, interoperability module 170 facilitates DME provider module 170 operating with other modules, such as health care professional module 120 and insurance module 150.

Medical conditions database 182 may refer to any suitable device capable of storing information associated with medical conditions. In certain embodiments, medical conditions database 182 may store various medical conditions, along with associated information, such as a formal medical name, an indication number, a key number, symptoms, diagnosis, treatment, associated prescriptions, or any other associated information. For example, medical conditions database 182 may include Current Procedural Terminology (CPT) codes, which may have a specific key number tied to a medical condition or procedure. As another example, medical conditions database 182 may include ICD-9-CM Diagnosis and Procedure Codes, which may have a specific key number tied to any medical condition or diagnosis. Providing a key number increases the exactness of a diagnoses medical condition. For example, if patient 135*a* simply included "diabetes" in the profile of patient 135, it is unclear whether that is type 1 diabetes, type 2 diabetes, or gestational diabetes. By including an exact key number, medical conditions database 182 provides further accurate and specific information regarding a medical condition. In some embodiments, interoperability module 140 may search medical conditions database 182 to find a medical condition to add to a user profile. For example, after a diagnosis, patient 135*a* or health care professional 135*b* may be adding a medical condition to the profile of patient 135*a*. Then, when a different user 135 (e.g., health care professional 135*b* or pharmacist 135*c*) views a profile of patient 135*a*, the most accurate description of the medical condition associated with patient 135*a* is provided.

NPI number database 183 may refer to any suitable device capable of storing information associated with a number of health care professionals 135*b*, pharmacists 135*c*, and pharmacies. In certain embodiments, NPI number database 183 may store information associated with the professionals, such as NPI number, name, NPI type, primary practice address, phone number, taxonomy, enumeration date, status, state, license number, or any other information associated with the professionals. In certain embodiments, interoperability module 140 may access and search through NPI database 183 to find health care professional 135*b*. For example, health care professional 135*b* may create a profile in interoperability module 140 and want to associate a NPI number with the profile. Interoperability module 140 may receive a search request from health care professional 135*b* (e.g., receive a last name), and then search NPI number database 183 for a match. Interoperability module 140 may display the matching results such that health care professional 135*b* may select among the results, and then associate the NPI number with the profile of health care professional 135*b*. By including a NPI number with a profile of user 135, interoperability module 140 provides additional verification that the professional is properly accredited based on the patient's needs. In some embodiments, interoperability module 140 may search NPI number database 183 for pharmacists 135*c*, pharmacy organizations, and/or individual pharmacy locations within a pharmacy organization.

DEA number database 184 may refer to any suitable device capable of storing information associated with a number of health care professionals 135*b*, pharmacies, or organizations authorized to prescribe certain controlled substances. In some embodiments, interoperability module 140 may access and search DEA number database 184 to find health care professional 135*b*. For example, health care professional 135*b* (e.g., a doctor) may create a profile in interoperability module 140 and want to associate a DEA number with the profile. Interoperability module 140 may receive a search request from health care professional 135*b* (e.g., receive a last name), and then search DEA number database 183 for a match. Interoperability module 140 may display the matching results such that health care professional 135*b* may select among the results, and then associate the DEA number with the profile of health care professional 135*b*. By including a DEA number with a profile of user 135, interoperability module 140 provides additional verification that the professional a patient may see is properly accredited based on the patient's needs.

NCPDP database 185 may refer to any suitable device capable of storing information associated with health care professionals 135*b*, pharmacists 135*c*, and pharmacies related to particular drugs and medications. NCPDP database 185 may have additional information related to health care professionals 135*b* and particular pharmacies. In some embodiments, interoperability module 140 may access data from NCPDP and store in memory 160 such that users 135*a* may associate the information with certain profiles or organizations.

NDC database 181 may refer to any suitable device capable of storing information associated with medications, drugs, and/or drug products. NDC database 181 may store unique and universal product identifiers (e.g., a three-segment number) for human drugs (e.g., prescription drugs, over-the-counter drugs, and insulin products) as well as information associated with the drug (e.g., manufacturer, product name, labeler, product, package size, or any information associated with the drug). In some embodiments, interoperability module 140 may access and search through NDC database 181 to identify certain drugs. For example, if patient 135*a* has a cold and buys cold medicine, patient 135*a* may scan in a barcode for and/or enter the cold medicine's NDC number. Interoperability module 140 may use the NDC number to search NDC database 181 and identify the specific medicine that patient 135*a* has purchased. Interoperability module 135 may further associate the NDC number (and/or corresponding drug information) to a profile of patient 135*a*. Continuing the example, if patient 135*a* seeks assistance from health care professional 135*b*, then health care professional 135*b* may view the profile of patient 135*a* and determine which drugs that patient 135*a* has taken in order to better assess the condition of patient 135*a*.

HCPCS database 186 may refer to any suitable device capable of storing information associated with medical supplies, durable medical goods, and/or medical devices. For example, there may be HCPCS numbers associated with medical devices like oxygen equipment and accessories, nebulizers, hospital beds, patient lifts, crutches, insulin pumps, or any other medical devices or equipment. HCPCS database 186 may store unique and universal product identifiers for medical devices and equipment that is not associated with any particular brand. For example, if patient 135*a* requires an insulin pump, interoperability module may determine the HCPCS number associated with the type of insulin pump needed. By using the HCPCS number associated with the insulin pump, interoperability module 140 ensures that the correct pump (e.g., with appropriate functionality) is selected. There may be many brands associated with a particular HCPCS number for the insulin pump. For example, the insurance of patient 135*a* may only cover certain brands of insulin pump, and interoperability module 140 may access API database 151 to determine which brands are covered.

Interoperability module 140 may refer to any suitable combination of hardware and/or software implemented in one or more modules to process data and provide the described functions and operations. In some embodiments, the functions and operations described herein may be performed by a pool of interoperability modules 140. In some embodiments, interoperability module 140 may include, for example, a mainframe, server, host computer, workstation, web server, file server, a personal computer such as a laptop, or any other suitable device operable to process data. In some embodiments, interoperability module 140 may execute any suitable operating system such as IBM's zSeries/Operating System (z/OS), MS-DOS, PC-DOS, MAC-OS, WINDOWS, UNIX, OpenVMS, or any other appropriate operating systems, including future operating systems.

In general, interoperability module 140 facilitates interoperability among modules and databases in system 100. Because information and electronic records within each module is often inaccessible or incompatible with other modules, interoperability module 140 may analyze the extracted data and create an electronic record in a different format that may be recognized by and compatible with another module. Interoperability module 140 may further transmit the new electronic record to the module such that it may accurately use the information to provide health care services. In some embodiments, interoperability module 140 may include processor 155, memory 160, and interface 165.

Memory 160 may refer to any suitable device capable of storing and facilitating retrieval of data and/or instructions. Examples of memory 160 include computer memory (for example, RAM or ROM), mass storage media (for example, a hard disk), removable storage media (for example, a CD or a DVD), database and/or network storage (for example, a server), and/or or any other volatile or non-volatile, non-transitory computer-readable memory devices that store one or more files, lists, tables, or other arrangements of information. Although FIG. 1 illustrates memory 160 as internal to interoperability module 140, it should be understood that memory 160 may be internal or external to interoperability module 140, depending on particular implementations. Also, memory 160 may be separate from or integral to other memory devices to achieve any suitable arrangement of memory devices for use in system 100.

Memory 160 is generally operable to store electronic records, profiles of users 135, profiles of organizations (e.g., pharmacies, DME providers, doctor's offices or groups), logic 162, and rules 164. Logic 162 generally refers to algorithms, code, tables, and/or other suitable instructions for performing the described functions and operations. Rules 164 generally refer to policies or directions for analyzing electronic records and data, extracting data from electronic records, creating electronic records using different data structures, and transmitting electronic records to various modules in system 100. Rules 164 may be predetermined or predefined, but may also be updated or amended based on the needs of patients, health care professionals, pharmacies, and insurance companies.

Memory 160 communicatively couples to processor 155. Processor 155 is generally operable to execute logic 162 stored in memory 160 to analyze electronic records having a particular data structure, extracting data from the electronic records, and creating additional electronic records in a format compatible with other modules in system 100, according to the disclosure. Processor 155 may comprise any suitable combination of hardware and software implemented in one or more modules to execute instructions and manipulate data to perform the described functions for interoperability module 140. In some embodiments, processor 155 may include, for example, one or more computers, one or more central processing units (CPUs), one or more microprocessors, one or more applications, and/or other logic.

In some embodiments, communication interface 165 (I/F) is communicatively coupled to processor 155 and may refer to any suitable device operable to receive input (e.g., electronic records and other health care data) for interoperability module 140, transmit output (e.g., reformatted electronic records and information) from interoperability module 140, perform suitable processing of the input or output or both, communicate to other devices, or any combination of the preceding. Communication interface 165 may include appropriate hardware (e.g., modem, network interface card, etc.) and software, including protocol conversion and data processing capabilities, to communicate through network 105 or other communication system that allows interoperability module 140 to communicate to other devices. Communication interface 165 may include one or more ports, conversion software, or both. In general, communication interface 165 may retrieve electronic records, profiles, and other data from memory 160, and may retrieve information from databases (e.g., medical conditions database 182, NPI number database 183, DEA number database 184, NCPDP database 185, and NDC database 181) and send information to health care modules (e.g., patient module 110, health care professional module 120, pharmacy module 130, insurance module 150, and DME provider module).

In operation, logic 162 and rules 164, upon execution by processor 155, facilitate interoperability among modules in system 100. Logic 162 and rules 164 also facilitate receiving electronic records from an organization, analyzing the electronic record, extracting data from the electronic record, and creating a second electronic record with a data structure that is compatible with another organization.

In some embodiments, interoperability module 140 receives a first electronic record from a first health care module, the first electronic record having a first data structure. The first health care module may be patient module 100, health care professional module 120, pharmacy module 130, DME provider module 170, insurance module 150, or any other health care module. Each module may have a particular data structure, form, format, or system for recording electronic information that is not compatible with other systems. Although electronic record contains patient information, due to the data format, another module may not be able to accurately read, access, or extract information from the first electronic record. For example, health care professional module 120 may transmit an electronic record containing prescription information. The data structure may be a written prescription that is scanned into health care professional module 120. Another module in system 100 may not be able to recognize the form, hand writing, or information contained in the prescription. As another example, insurance module 150 may contain its insurance information for a patient using particular codes and code numbers regarding the plan, prescriptions, and coverage. Another module in system 100 may not recognize the structure or be able to determine coverage information from the electronic record of insurance module 150. Thus, interoperability module 140 may receive the electronic records before transmitting to the intended recipient module.

In some embodiments, interoperability module 140 receives a third electronic record from a first health care database, the third electronic record having a third data structure. The health care database may be medical conditions database 182, NPI number database 183, DEA number database 184, NCPDP database 185, and NDC database 181, or any other health care database. Interoperability module 140 may access these databases to receive additional information. For example, when setting up a patient profile, interoperability module 140 may add and associate medical conditions to a patient profile. The information contained in medical conditions database 182 may be in a particular format that is not recognizable by or compatible with other health care modules, and/or contain superfluous information that is not required. As another example, when interoperability module 140 creates a health care professional profile, it may add information from registered websites such as the NPI number database 183 and DEA number database 184. Other health care modules may not understand the significance of the numbers being associated with a health care professional profile and thus interoperability module 140 may first receive the information to determine its significance.

In some embodiments, interoperability module 140 analyzes the first electronic record having the first data structure. Interoperability module 140 may analyze the record to determine the information that it contains and the significance of the data. For example, if health care professional module 120 transmits a prescription for a drug or medical device, interoperability module 140 may determine the medication, type of device, dosage, and/or instructions associated with the prescriptions. As another example, if interoperability module 140 accesses NPI number database 183, it may determine that a NPI number does not exist for a health care professional.

In some embodiments, interoperability module 140, based on the analysis, extracts a portion of data from the first electronic record. Interoperability module 140 may only extract information relevant to other modules in system 100. For example, when accessing NPI number database 183, it may extract certain information associated with a health care professionals profile (e.g., address, taxonomy, registration information), but not other information (NPI number itself) that is not relevant to the other system modules.

In some embodiments, interoperability module 140 creates a second electronic record using the portion of data from the first electronic record, the second electronic record having a second data structure, and the second data structure is configured to be compatible with a second health care module. Interoperability module 140 may have a uniform second data structure that is compatible with each module of system 100. For example, interoperability module 140 may take the extracted data and add it to a particular user profile, such that the modules may access and extract data from the profiles. In some embodiments, interoperability module 140 may create a unique second data structure that is compatible only with a specific second health care module. For example, when sending prescription information to pharmacy module 130, interoperability module 140 may populate a specific electronic form required by pharmacy module 130 to process and fulfill the prescription.

In some embodiments, interoperability module 140 is further configured to transmit the second electronic record to the second health care module. If the second data format is unique to the second heath care module, then the electronic record itself may be sent and then analyzed internally by the second health care module. If the second data format is universal for all health care modules, interoperability module 140 may display the data and/or transmit. For example, if the second electronic record is contained within a user profile, the health care module may access the data by viewing the profile itself, rather than receiving the electronic record.

In some embodiments, interoperability module 140 facilitates creating profiles for users 135 and organizations (e.g., pharmacies, doctor's offices, DME providers) that may be viewed, accessed, and associated with modules in system 100 and/or other profiles. Profiles may store and incorporate information for users 135 or organizations that may be useful for other users 135. As examples, a profile for patient 135a may include name, photo, date of birth, medical conditions, allergies, vaccinations, active prescriptions (e.g., from all pharmacies), insurance companies (and associated profile), preferred pharmacies (and associated profiles), emergency contacts (and associated profiles), or any other information related to patient 135a. As another example, a profile for health care professional 135b may include name, specialty, NPI number, and DEA number. Further, a profile for pharmacist 135c may include name, pharmacy affiliation (e.g., large pharmacy brand or physical pharmacy store or location), and NPI number. Finally, interoperability module 140 may facilitate creating profiles for organizations in system 100. For example, pharmacy brand may have a profile (e.g., CVS, Walgreens) and each individual location (e.g., CVS pharmacy on 123 Main Street) may have a profile. In this example, interoperability module 140 may associate the profile of patient 135a with the profile of a specific pharmacy to indicate that is the preferred pharmacy location to have prescriptions filled. By associating profiles, interoperability module 140 may recognize the pharmacy as a preferred pharmacy for patient 135a, and facilitate health care professional module 120 automatically transmitting a prescription to the correct pharmacy for patient 135a.

Profiles may organize all important health information for patient 135a in an efficient and easily tracked manner. Other modules or users (e.g., health care professional module 120 and/or health care professional 135b) may access a profile of patient 135a to retrieve information about patient 135a. For example, interoperability module 140 may facilitate health care professional module 120 retrieving insurance information from the profile of patient 135a so that health care professional module 120 may incorporate that information into its billing process, thereby conserving computational resources and bandwidth expended in gathering the information during a visit of patient 135a to the office and/or contacting an insurance company directly.

Figure 2:
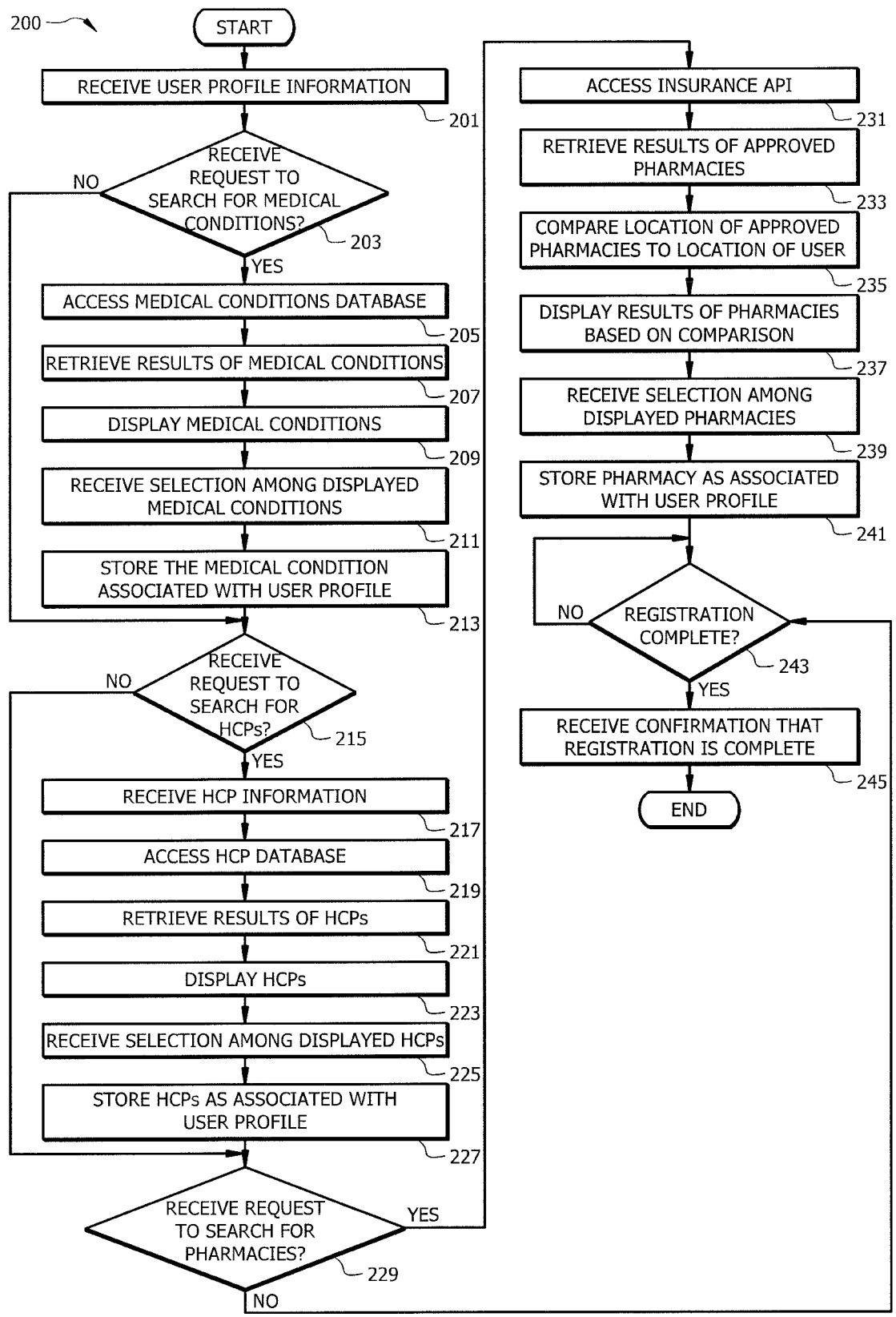
FIG. 2 illustrates an example flowchart for a method for various users of a system to register and create user profiles to facilitate interoperability among health care modules.

By creating profiles for patient 135a, interoperability module 140 may facilitate patient 135a sharing their health information with other modules or users 135 such that each has the most up-to-date health information of patient 135a. In some embodiments, profiles may have various levels of restriction and access. For example, a profile of patient 135a may not be accessed by another patient 135a in system 100 without permission being granted first. In some embodiments, only a portion of a profile of patient 135a may be accessed. For example, interoperability module 140 may provide insurance module 150 access to portions of a profile, such as a name, insurance information, associated health care professionals 135b, and prescription information of patient 135a, but will not provide access to more private aspects such as medical conditions and prescriptions unrelated to insurance. The process interoperability module 140 may use to create, establish, and add information to profiles for various users 135 is shown in FIG. 2 and discussed in more detail below.

In some embodiments, interoperability module 140 accesses information from database(s) in system 100, extracts relevant information, and creates an electronic record in an appropriate format for a specific module. For example, interoperability module 140 may analyze the information provided by NPI number database 183, and extract certain information from NPI number database 183 based on the analysis. For example, interoperability module 140 may retrieve only address and contact information for a pharmacy, rather than all information associated with the pharmacy. Interoperability module 140 may further create a data format for the extracted information in the form that may be accessed by various modules in system 100. For example, interoperability module 140 may use the retrieved information to create a profile for the pharmacy or provide a contact information record to be sent to another module. Interoperability module 140 may access and extract information from any of the databases in system 100, and create an electronic record in an appropriate format for any module of system 100.

In some embodiments, interoperability module 140 facilitates tracking and storing information related to medications, food, or other items ingested by patient 135a. Interoperability module 140 may receive information through patient module 110 and/or user device 115a, for example, scanning in a bar code on a food item or providing a NDC number of a medication. This may provide an efficient way for patient 135a to incorporate additional health information into the profile of patient 135a, and to provide a complete view of the health of patient to other users 135 in system 100. For example, by scanning all over-the-counter products, interoperability module 140 may determine whether any of the products may have an interaction with a prescription being taken. Interoperability module may alert patient 135a through patient module 110 not to use or purchase an over-the-counter product while taking a certain prescription saved in a user profile.

In certain embodiments, interoperability module 140 may facilitate storing information about and managing all prescriptions of patient 135a in the profile. The profile may include information about each prescription, such as name, status, associated pharmacy, associated health care professional(s) 135b, photos, dosage instructions, or any other information related to the prescription. By storing information about all prescriptions in one profile, patient 135a may readily access and manage the prescriptions. For example, the user profile of patient 135a in interoperability module 140 may facilitate transferring prescriptions to one or more pharmacies, submitting a request for a refill to health care professional module 120 and/or pharmacy module 130, and access any information about prescriptions. As an example, patient 135a may utilize patient module 110 to review prescription information and request any changes or refills that may be transmitted to health care professional module 120 by interoperability module 140, rather than patient 135a having to call or otherwise contact health care professional 135b to make any changes. Interoperability module 140 provides an efficient management, storage, and editing technique regarding prescriptions.

Figure 3:
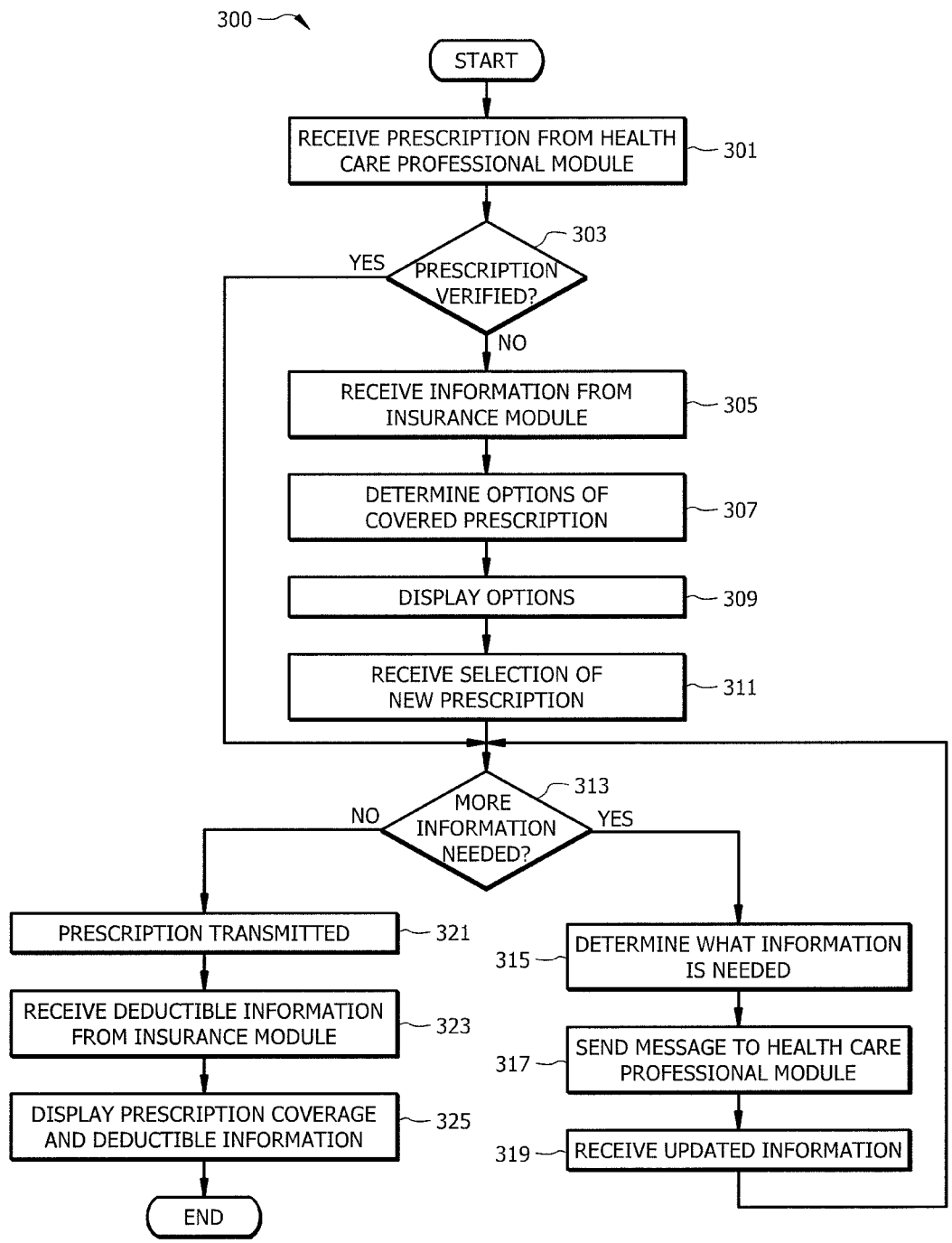
FIG. 3 illustrates an example flowchart for facilitating interoperability between a health care professional module and an insurance module.
Figure 4:
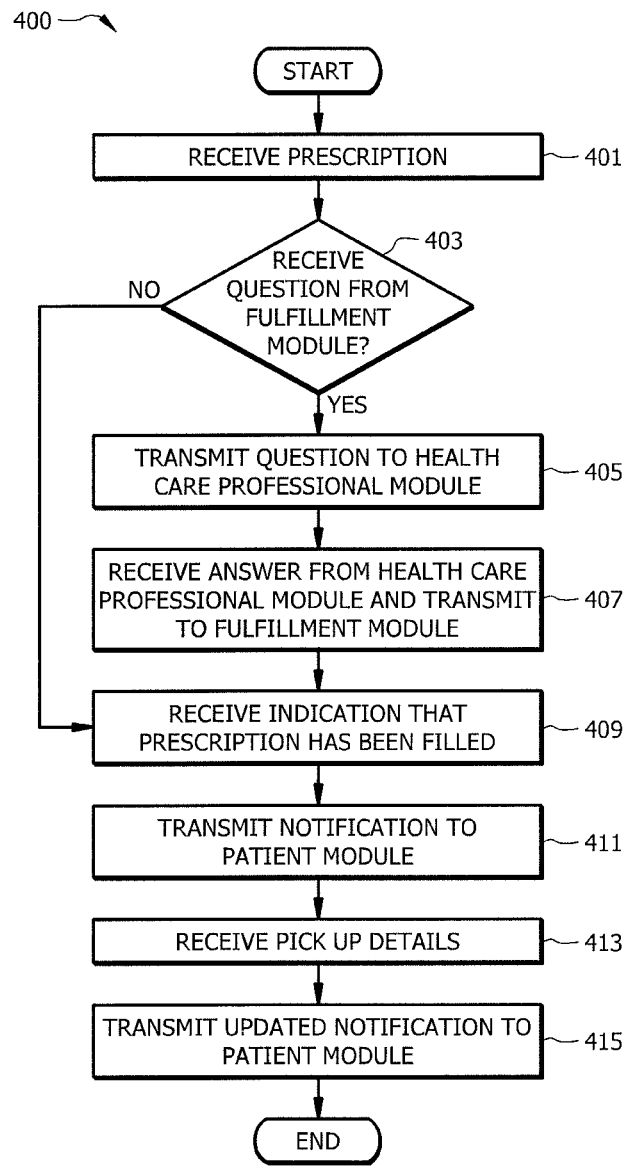
FIG. 4 illustrates an example flowchart for facilitating interoperability between a pharmacy module and health care professional module.

In certain embodiments, interoperability module 140 may process a prescription for patient 135a by health care professional 135b. Interoperability module 140 may receive prescription information from health care professional module 120. In some embodiments, interoperability module 140 may access API database 151 to determine whether a prescription is covered by insurance of patient 135a, and determine co-pay and deductible information automatically. Interoperability module 140 may provide this information to health care professional module 120 and/or patient module 110 so that patient 135a and/or health care professional 135b may receive real time feedback about whether a prescription is covered or not. In some embodiments, interoperability module 140 may determine alternative prescriptions that would provide the same treatment. Interoperability module 140 may access NDC database 181, medical conditions database 182, or another database to determine alternative prescriptions. As an example, if health care professional 135b submits a name-brand prescription, interoperability module 140 may determine that the name-brand is not covered by the insurance of patient 135a and provide alternative prescriptions that provide the same treatment and are covered by insurance. The process interoperability module 140 may use to manage prescriptions for patients 135a is shown in FIG. 3 and FIG. 4, as discussed in more detail below.

Interoperability module 140 may further transmit a prescription for medication or medical device to pharmacy module 130 and/or DME provider module 170. Interoperability module 140 may transmit the prescription to pharmacy module 130 in response to determining whether insurance covers the prescription. Interoperability module 140 may receive information from health care professional module 120 as an electronic record and translate it into a record format compatible with pharmacy module 130. For example, health care professional 135b may scan in a written prescription, analyze the writing, and extract the data that needs to be provided to pharmacy module 130. Interoperability module 140 may further extract information from the profile of health care professional 135b and combine it with the data extracted from the prescription received from health care professional module 120. Interoperability module 140 may create an additional electronic record in a format compatible with pharmacy module 130 and then transmit the prescription to pharmacy module 130 such that an associated pharmacy may fulfill the prescription for patient 135. By creating an electronic record in an appropriate format with the required information, interoperability module 140 facilitates communication between health care professional module 120 and pharmacy module 130 without concern for compatibility. Interoperability module 140 extracts only necessary data, thereby conserving computational resources, bandwidth, and memory that would be consumed by each module reentering the data for the prescription and maintaining a duplicate copy of the electronic record for the prescription.

In certain embodiments, interoperability module 170 determines insurance coverage for particular prescriptions and facilitates exchange of insurance information. For example, interoperability module 170 may access API database 151 from insurance module 150 to get payment and deductible information for patient 135a. interoperability module 170 may provide the necessary data from API database 151 to pharmacy module 130 and/or DME provider module 170 such that a pharmacy and/or DME provider may prepare and fulfill the medical equipment and/or prescription for patient 135a and have deductible information in order to charge patient 135a an appropriate amount for the medical equipment.

In particular embodiments, interoperability module 140 may provide updates on the status of a prescription. Interoperability module 140 may provide updates to patient 135a (e.g., through patient module 110 and/or an alert or message to user device 115a). Status updates may include, for example, "new prescription on file," when a new prescription is added; "being filled," when a pharmacy accepted the order and started preparing it; "ready for pickup," notifying user 135 that an order is complete and patient 135a may pick it up from the pharmacy; "needs to be discussed," indicating there are some questions about the prescription that prevent pharmacy from fulfilling it; "filled;" indicating patient 135a has received the prescription and is using it as prescribed, or any other status update that may be useful for user 135 to know. Interoperability module 140 may provide status updates to any user 135 in system 100 through the respective module. For example, health care professional 135b may receive updates through health care professional module 120 by accessing a profile of patient 135a. Pharmacist 135c may receive updates through pharmacy module 130, and/or may be able to generate reports about the outstanding prescriptions at a particular pharmacy location.

In some embodiments, interoperability module 140 may facilitate transferring a prescription from one pharmacy to another. Interoperability module 140 may initiate a transfer based on a change in insurance information of patient 135a. For example, if the insurance of patient 135a changes such that prescriptions may only be filled by a certain pharmacy organization, interoperability module 140 may transfer the prescription such that it is filled by a pharmacy associated with the insurance. In some embodiments, interoperability module 140 may receive a request from user 135 (e.g., patient 135a, health care professional 135b) via a module (e.g., patient module 110 and/or health care professional module 120) to transfer the prescription. Interoperability module 140 may transfer the prescription by sending an electronic record containing the information about the prescription to pharmacy module 130 associated with the new pharmacy. In some embodiments, interoperability module 140 may also notify the old pharmacy through the associated pharmacy module 130 that the prescription has been transferred.

In particular embodiments, interoperability module 140 facilitates transmitting messages among modules in system 100. Interoperability module 140 may provide access to a messaging center for all modules in system 100. The messaging center may facilitate communication among the modules by allowing each to create a conversation with another. For example, interoperability module 140 facilitates pharmacist 135 accessing messaging center through pharmacy module 130 and creating a new conversation with health care professional 135b through health care professional module 120. Interoperability module 140 transmits messages back and forth such that pharmacist 135c and health care professional 135b may be in real-time communication. Interoperability module 140 may further facilitate a group conversation, for example, to loop in patient 135a and/or insurance agent 135d. Messages may include a "read" or "unread" identification notifying user 135 about a new query. Interoperability module 140 may include standard responses to facilitate faster and more efficient communication. Interoperability module 140 may provide a health care professional 135b a standard response of "approved" or "switch to generic" that would be repeatedly used, thereby conserving time between answers. In some embodiments, messages may be saved until accessed or changed by the appropriate user 135.

In some embodiments, interoperability module 140 may generate a report regarding prescriptions of patient 135a. Interoperability module 140 may access the profile of patient 135a and review any information about prescriptions of patient 135a. Information about prescriptions can include filled prescriptions, cost of the filled prescriptions, prescriptions in other statuses (e.g., being filled, ready for pick-up), and estimated costs for open but not filled prescriptions. Interoperability module 140 may further access information about fulfillment centers and their contacts (e.g., pharmacist 135). In some embodiments, interoperability module 140 may generate the report in response to receiving a request. The request may be received from a module in system 100 (e.g., insurance module 150), and may include information such as a time period for the report (e.g., the past 24 hours, the past week, the past 30 days, the past 90 days, the past year, or any time period). In some embodiments, interoperability module 140 may transmit the report to insurance module 150, patient module 110, health care professional module 120, and/or pharmacy module 130.

A component of system 100 may include an interface, logic, memory, and/or other suitable element. An interface receives input, sends output, processes the input and/or output and/or performs other suitable operations. An interface may comprise hardware and/or software. Logic performs the operation of the component, for example, logic executes instructions to generate output from input. Logic may include hardware, software, and/or other logic. Logic may be encoded in one or more tangible media, such as a computer-readable medium or any other suitable tangible medium, and may perform operations when executed by a computer. Certain logic, such as a processor, may manage the operation of a component. Examples of a processor include one or more computers, one or more microprocessors, one or more applications, and/or other logic.

Modifications, additions, or omissions may be made to the systems described herein without departing from the scope of the disclosure. For example, system 100 may include any number of patient modules 110, health care professional modules 120, pharmacy modules 130, DME provider modules 170, insurance modules 150, medical conditions database 182, NPI number database 183, DEA number database 184, NCPDP database 185, and NDC database 181. As another example, particular functions, such as analyzing data from databases and creating new electronic records in a format compatible with modules may be performed by a separate component and interoperability module 140 receives the information regarding the analysis and/or electronic records. The components may be integrated or separated. Moreover, the operations may be performed by more, fewer, or other components. Additionally, the operations may be performed using any suitable logic comprising software, hardware, and/or other logic. As used in this document, "each" refers to each member of a set or each member of a subset of a set.

FIG. 2 illustrates an example flowchart for a method 200 for various users 135 of system 100 to register and create user profiles to facilitate interoperability among health care modules. In general, method 200 facilitates various users 135 of interoperability module 140 of FIG. 1 registering and creating user profiles. Method 200 may be performed by interoperability module 140, or any other component of system 100. Method 200 may apply to the creation of a profile of any user 135 or organization of FIG. 1, such as patients 135a, health care professionals 135b, pharmacists or fulfillment employees 135c, insurance or payee employees 135d, or DME provider employees 135e, pharmacies associated with pharmacy module 130, offices associated with health care professional module 120, insurance companies associated with insurance module 150, or any other user or organization of system 100. The steps of method 200 may be repeated as necessary to receive all the information to provide and facilitate interoperability between various health care modules. By registering various users 135, interoperability module 140 may store data in an efficient manner, thus conserving computational resources and allowing for faster processing speed.

Method 200 begins at step 201, in some embodiments, where interoperability module 140 receives user profile information. User profile information may be any information related to the user. For example, user profile information may be name, address, date of birth, employment information or any other information related to the user. In some embodiments, a user may be a caregiver that cares for multiple patients. Continuing the example, the caregiver may include information about the caregiver himself as well as information about the one or more patients the caregiver may take care of. As another example, the user may be health care professional 135b, such as a doctor, nurse practitioner, physician's assistant, nurse or administrative assistant at a health care professional's office. In some embodiments, patient 135a may submit general health information beyond prescription information, such as medical history, and exercise and diet. In some embodiments, interoperability module 140 may receive information about specific foods and medications taken by patient 135a. Patient 135a may input the information by scanning barcodes of certain food items, so that the general food intake may be tracked and viewed by other users 135 (e.g., health care professional 135b) of system 100. By collecting the user profile information, interoperability module 140 may register each user such that the various health care modules may efficiently communicate and share data.

In general, at steps 203, 215 and 229, in some embodiments, interoperability module 140 determines whether it receives requests to search for specific issues that may be included in a user profile. At each step, this determination may prompt interoperability module 140 to search external databases or internal databases to determine and potentially add certain information to a user profile. Adding information to profiles from external databases provides an efficient way to maintain and share data in the common format among the different health care modules.

At step 203, in some embodiments, interoperability module 140 determines whether there is a request to search for medical conditions. The request may be received through network 105 from user device 115 that submits the request. The request may appear as a pop up on the screen that solicits whether the user wants to search for medical conditions to add to the user's profile. In some embodiments, medical conditions may be a condition that a patient has, a condition that a patient has had in the past, a condition that a health care professional is an expert in, a condition that an insurance company provides financial coverage for, a condition that a durable medical provider can provide equipment for, or any other information related to the medical condition. If at step 203, interoperability module 140 determines there has not been a request to search for medical conditions, interoperability module 140 continues from step 215, discussed below. If at step 203, interoperability module 140 determines there has been a request to search for medical conditions, interoperability module 140 may access medical conditions database 182 in step 205. This database may be stored internally or externally from interoperability module 140. In accessing medical conditions database 182, interoperability module 140 may use the information included in the request to determine any inputs to search the medical database. Interoperability module 140 may perform a comparative analysis to determine which medical conditions are relevant or match the medical condition input by the request in step 203.

At step 207, in some embodiments, interoperability module 140 retrieves the results of the various medical conditions and displays the medical conditions at step 209. These medical conditions may be displayed on user device 115 such as a drop down menu that user may view and select among. At step 211, in some embodiments, interoperability module 140 receives the selection among the displayed medical conditions. For example, user 135 may select one or more medical conditions to associate with the user profile. At step 213, in some embodiments, interoperability module 140 stores the medical condition to associate with the user profile. In some embodiments, a caregiver may be creating a user profile for the patient the caregiver takes care of Thus, caregiver 135*a* may be able to associate the medical condition with one or more patient user profiles. In some embodiments, health care professional 135*b* may be adding information to an existing user profile. For example, if patient 135*a* has visited with health care professional 135*b* and determined that patient 135*a* has a medical condition, then health care professional 135*b* may add it to the user profile of patient 135*a*. By adding medical conditions to a user profile, patient 135*a* may have access to information about that medical condition, such as symptoms, warnings, when to call a health care professional for help, certain drugs that may be taken to alleviate certain symptoms, as well as any other information that may be helpful to a user. In some embodiments, other health care professionals 135*b* may be able to access a user profile and determine that a user profile is associated with a specific medical condition. This may impact the medications prescribed to the user as well as various treatment techniques provided by other health care professionals.

At step 215, in some embodiments, interoperability module 140 determines whether there is a request to search for health care professionals. Interoperability module 140 may determine that a user profile is being created, and thus may communicate a prompt to user device requesting whether to add a health care professional to the user profile. The request may also include information for the health care professional, such as NPI number, DEA number, name, address, or any other identifying information. This information may be helpful in searching for the health care professional in a database. If at step 215, interoperability module 140 determines that a request to search for a health care professional is not received, the method continues to step 229, discussed below. If at step 215, interoperability module 140 receives a request to search for a health care professional, the method continues to step 217 where interoperability module 140 receives health care professional's information. The health care professional's information may be included with the request.

Once interoperability module 140 receives the health care professional's information at step 217, interoperability module 140 accesses a health care professional database at step 219. The health care professional database may be an NPI database 183, DEA number database 184, a state registry for health care professionals, or any other database that may have information about health care professionals. In accessing the health care professional database, interoperability module 140 may compare the health care professional information received at step 217 to the information in the one or more databases. At step 221, interoperability module 140 may retrieve results of the health care professional from the one or more databases and display the various health care professionals at step 223. At step 225, in some embodiments, interoperability module 140 may receive a selection among the displayed health care professional from step 223. The user may filter through the different health care professional information displayed at step 223 and select one or more to associate with the user's profile.

At step 227, interoperability module 140 stores the health care professional as associated with the user profile. By associating one or more health care professionals with the user profile, user 135 may have information about their health care professional 135*b* readily available. For example, user may need to call or send a message to health care professional 135*b* for a question and have the phone number available for access. As another example, another health care professional 135*b* may want to see information from another health care professionals 135*b* that patient 135*a* visits and can access that information through the user's profile. As another example, a pharmacy or fulfillment organization may want to see the doctor that prescribed patient 135*a* a specific prescription and may readily determine that information by accessing a profile of patient 135*a* and seeing which health care professionals 135*b* are associated with that user profile.

In some embodiments, steps 215 through 227 may be used by health care professionals to create a health care professional profile. Health care professional 135*b* may then have her own profile such that other users can associate their profile(s) with the health care professional profile more readily. In some embodiments, when creating a health care professional profile, interoperability module 140 may access multiple databases to ensure that the health care professional is a registered professional with proper accreditation. For example, interoperability module 140 may determine whether health care professional 135*b* has the ability to prescribe certain prescriptions and medications required by patient 135*a* based on the patient's medical conditions. For example, in order to prescribe certain medications, a health care professional must be registered with the Drug Enforcement Administration and have a DEA number that can be verified by searching DEA number database 184.

At step 220, in some embodiments, interoperability module 140 determines whether there is a request to search for pharmacies. In some embodiments, step 229 implements some of the techniques performed at steps 215 and 203. If at step 229, interoperability module 140 has not received a request to search for pharmacies, interoperability module 140 continues to step 243, described below. If at step 229 interoperability module 140 receives a request to search for pharmacies, the method continues from step 231.

At step 231, in some embodiments, interoperability module 140 accesses insurance company information from API database 151. API database 151 may include information about coverage for patient 135*a* as well as approved pharmacies. In order for user 135 to associate with one or more pharmacies, interoperability module 140 may access the insurance information of user 135*a* to determine which pharmacies may be best suited for patient 135*a* and/or health care professional 135*b* to utilize in fulfilling prescriptions. At step 233, interoperability module 140 may retrieve the results of the approved pharmacies. Accordingly, user 135 may only fill prescriptions at approved pharmacies and thus reduce the risk of filling prescriptions at a pharmacy that is not covered and having to pay additional expenses.

In some embodiments, interoperability module 140 may use the location of user 135 to determine the most suitable pharmacy. At step 235, in some embodiments, interoperability module 140 compares the location of approved pharmacies retrieved in step 233 to the location of the user. The location of user 135 may be the current location of user 135 as determined using location information of user device 115, an address associated with the user profile (e.g., a patient's home or place of work), or any other location preference. In this comparison, interoperability module 140 may determine the approved pharmacies that are in the appropriate radius of the location of user 135. At step 237, interoperability module 140 may display the results of the pharmacies based on the comparison. When the results are displayed, user 135 may, for example, select one or more pharmacies using a drop-down menu and click on the pharmacies to add. At step 239, in some embodiments, interoperability module 140 receives the selection among the displayed pharmacies, and at step 241, stores the pharmacy or pharmacies as associated with the profile of user 135. By associating pharmacies with a user profile, other health care professionals 135b may access that information to fill prescriptions efficiently. For example, health care professional 135b who is refilling a prescription may submit the refill request through health care professional module 120 such that interoperability module 140 determines the closest pharmacy to user 135b and automatically transmits the prescription to the associated pharmacy module 130. For example, if the user is out of state and needs the prescription, the prescription may be automatically sent to the nearest pharmacy for user 135. As another example, user 135 may preference certain pharmacies for certain health care professionals 135b. In some embodiments, user 135 may associate one or more pharmacies with the user profile. As another example, if the user profile is being created for an insurance company, the insurance company may associate various pharmacies with the insurance company's user profile. In that way, patient 135a, health care professional 135b, or pharmacist 135c may see whether the insurance company is associated with a specific pharmacy and whether prescriptions may be filled there. For example, one insurance company may only fill prescriptions at a CVS while another may only use Walgreens. When submitting a prescription to a pharmacy, health care professional 135b may want to understand what pharmacies are covered by a patient's insurance before submitting the prescription.

Finally, at step 243, in some embodiments, interoperability module 140 determines whether registration is complete. Interoperability module 140 may display a prompt on the screen of user device 115 asking whether user 135 has completed registration. User 135 may select that registration is complete and interoperability module 140 may receive confirmation that registration is complete in step 245. In receiving confirmation, interoperability module 140 may save all newly received data and properly associate received information with the user profile such that others in the system may be able to access the associated information.

Modifications, additions, or omissions may be made to the methods described herein without departing from the scope of the disclosure. For example, the steps may be combined, modified, or deleted where appropriate, and additional steps may be added. For example, steps 243 and 245 may be omitted; rather than query whether registration is complete, interoperability module 140 may automatically save the results and profile elements received. Additionally, the steps may be performed in any suitable order without departing from the scope of the present disclosure. For example, searching for associated pharmacies at steps 229-241 may begin the registration process and thus occur before step 203. While discussed as interoperability module 140 performing the steps, any suitable component of system 100 may perform one or more steps of the method.

FIG. 3 illustrates an example flowchart for method 300 for facilitating interoperability between health care professional module 120 and insurance module 150. In general, method 300 illustrates determining whether a drug prescription is covered by a patient's insurance. By providing that information to health care professional 135b through health care professional module 120, health care professional 135b may make changes to the prescription before submitting it for fulfillment. For example, if health care professional 135b prescribes the name brand of the prescription, interoperability module 140 may determine that the prescription is not covered by the patient's insurance and provide an alert. Continuing the example, after receiving the alert, health care professional 135b may alter the prescription to a generic drug that is covered by a patient's insurance. Thus, method 300 provides for a more efficient way to determine prescription coverage and reduce the likelihood that a prescription is not covered by a patient's insurance; thereby conserving resources and not sending multiple requests for insurance information and fulfilling incorrect prescriptions.

Method 300 begins at step 301, in some embodiments, where interoperability module 140 receives the prescription from health care professional module 120. Interoperability module 140 may receive the prescription by accessing it in a patient's electronic health records, receiving entry of new prescription information, or receiving an RX barcode from a prescription label or box. When interoperability module 140 receives the prescription, it may receive information about the drug including the ingredients, side effects, conditions it is meant to treat, and any other information that may be useful for health care professional 135b or patient 135a. The prescription may also include directions for taking the prescription such as number of doses, times per day, items to consume with the prescription, as well as items to avoid. Interoperability module 140 may receive the prescription in a particular data format that requires analysis to extract the relevant information. Interoperability module 140 may analyze the contents of the received prescription and extract portions of the data such that the prescription may be processed.

At step 303, in some embodiments, interoperability module 140 determines whether the prescription is verified or covered by a patient's insurance. If, at step 303 interoperability module 140 determines the prescription is covered, method 300 continues to step 313, discussed below. If interoperability module 140 determines the prescription is not covered at step 303, the method continues from step 305, in some embodiments. In order to verify the prescription, interoperability module 140 may, at step 305 receive information from the insurance company, such as information from API database 151 that provides details about the insurance coverage of patient 135a and prescription drug details. Interoperability module 140 may access API information from a patient's insurance to determine whether the prescription is covered by the patient's insurance. Interoperability module 140 may store this information in a memory (e.g., memory 160 of FIG. 1); thereby conserving computational resources and not accessing API database 151 each time the prescription is refilled. Instead, interoperability module 140 may store an indication that a prescription is covered, and then periodically check API database 151 to determine whether any changes in insurance have occurred.

At step 307, in some embodiments, interoperability module 140 determines options of covered prescriptions related to the prescription received in step 301. Interoperability module 140 may analyze the API information to determine what drugs would be covered by the insurance company and further determine what drugs are appropriate replacements for the prescription that was submitted. Interoperability module 140 may access information from a database that indicates corresponding or replacement medications for certain other types of medications. Interoperability module 140 may then compare the medications to determine an appropriate replacement. At step 309, in some embodiments, interoperability module 140 displays the options determined in step 307. These options and information regarding the drugs may be displayed to health care professional 135*b* through health care professional module 120, such that a replacement prescription may be selected from among the various options for an adequate replacement prescription. At step 311, in some embodiments, interoperability module 140 receives selection of the new prescription from the options displayed in step 309 on a screen, and determines that selection is the prescription to be filled. Interoperability module 140 may further receive information about the prescription such as coverage information, deductible information, side effects information, and/or any other information related to the drugs and prescription.

Interoperability module 140 then determines whether more information is needed before filling a prescription at step 313. Interoperability module 140 may determine it requires additional patient information, prescription information, drug dosage and usage requirements, instructions, medical conditions suffered by the patient, or any other information that may be required such that the prescription may be fulfilled by a pharmacy and used by patient 135*a*. If at step 313, interoperability module 140 determines that more information is not needed, method continues to step 321, discussed below. If at step 313, interoperability module 140 determines that more information is needed, method 300 continues from step 315 where interoperability module 140 determines what information is needed. Interoperability module 140 may have access to certain information or permissions a pharmacy must have before filling a prescription. By performing a check on this information and/or permissions before sending the prescription for fulfillment, interoperability module 140 conserves bandwidth that would be expended by having to pause a fulfillment once it is has been transmitted to pharmacy module 130. At step 317, in some embodiments, interoperability module 140 sends a message to health care professional 135*b* via health care professional module 120 on the information that is needed and then receives the updated information in step 319. Health care professional 135*b* may enter this information through user device 115*b*. In some embodiments, method 300 may analyze and extract the information and create a new electronic record in a format that will be compatible with pharmacy module 130.

Method 300 continues to step 321 where interoperability module 140 transmits the prescription. The prescription may be transmitted to patient module 110 so that patient 135*a* may determine what health care professional 135*b* prescribed to them, as well as information about the prescription. The prescription may also be transmitted to pharmacy module 130 or other fulfillment organization such that the prescription may be filled for patient 135*a* to come pick up.

At step 323, in some embodiments, interoperability module 140 receives deductible information from the insurance company. Interoperability module 140 may send a request for the information such it receives the deductible information for this prescription. Interoperability module 140 may also determine the deductible information based on the API database 151 information accessed and/or stored in its system. At step 325, in some embodiments, interoperability module 140 displays prescription coverage and deductible information. This may be displayed to patient 135*a*, the insurance company agent 135*d*, as well as the pharmacist 135 via patient module 110, insurance module 150, and pharmacy module 130, respectively. After this, the method ends.

Modifications, additions, or omissions may be made to the methods described herein without departing from the scope of the disclosure. For example, the steps may be combined, modified, or deleted where appropriate, and additional steps may be added. Steps 303 and 305 may be combined such that the prescription is verified based on the information received from insurance module 150. Additionally, the steps may be performed in any suitable order without departing from the scope of the present disclosure. For example, receiving deductible information from insurance module 150 at step 323 may occur before the prescription is transmitted in step 321. While discussed as interoperability module 140 performing the steps, any suitable component of system 100 may perform one or more steps of the method.

FIG. 4 illustrates an example flowchart for method 400 facilitating interoperability between pharmacy module 130 and health care professional module 120. In general, method 400 allows for interoperability between different systems in the healthcare industry, specifically it involves prescription management and facilitating a prescription being accurately and timely fulfilled by a pharmacy or fulfillment company. By facilitating interaction between a health care professional system and a fulfillment company, method 400 conserves computational resources as well as bandwidth expended by transmitting incompatible electronic records or files.

Method 400 begins at step 401, in some embodiments, where interoperability module 140 receives the prescription information. The prescription information may include coverage information such as a patient's insurance coverage as well as deductible information. The deductible information may indicate how much a fulfillment company should charge patient 135*a* when retrieving the filled prescription. In some embodiments, interoperability module 140 may further transmit the prescription information to pharmacy module 130 and/or DME provider module 170 for filling.

At step 403, in some embodiments, interoperability module 140 determines whether it has received a question from fulfillment module 130 and/or DME provider 170. Interoperability module 140 may continually assesses whether fulfillment module 130 sends and/or may check for questions at certain intervals. In some embodiments, interoperability module 140 may analyze the received question to determine where to transmit the inquiry. For example, interoperability module 140 may determine health care professional 135*b* is associated with the prescription. Interoperability module 140 may further determine the information needed by fulfillment module 130 based on the question submitted. If interoperability module 140 determines that a question has not been received after a certain period of time, method 400 continues to step 409, as discussed below. If at step 403, interoperability module 140 determines that a question has been received from fulfillment module 130, method 400 continues to step 405. At step 405, in some embodiments, interoperability module 140 transmits the question to health care professional module 120. In some embodiments, the system of electronic records for fulfillment module 130 and health care professional module 120 may be incompatible such that the information may not be accurately received. Interoperability module 140 may extract information from the question from fulfillment module 130 and create a new electronic record in a format compatible with health care professional module 120. At this point, health care professional module 120 may receive the question and determine any answer. Health care professional 135b may enter the answer through user device 115 in a particular format or data structure. At step 407, in some embodiments, interoperability module 140 receives the answer from health care professional 135b, for example, and transmits the answer to fulfillment module 130. In certain embodiments, step 403 and 407 may be repeated until fulfillment module 130 receives answers to all of the questions to fill a prescription.

At step 409, in some embodiments, interoperability module 140 receives an indication that the prescription has been filled. Interoperability module 140 may receive this indication from fulfillment module 130. In some embodiments, interoperability module 140 may automatically receive an indication from the fulfillment module 130, which may be programmed to send an automatic alert to interoperability module 140.

Method 400 continues at step 411, in some embodiments, where interoperability module 140 notifies user 135 that the prescription has been filled. At step 413, in some embodiments, interoperability module 140 receives pickup details from fulfillment module 130 regarding when and how user 135 should pick up the prescription. For example, the notification may indicate that user 135 must bring a form of identification in order to pick up the prescription. As another example, the notification may indicate the time that the prescription will be available as well as the pharmacy that has fulfilled the prescription, including pharmacy hours and details. Once interoperability module 140 receives the pickup details at step 413, interoperability module 140 may transmit the updated notification to user 135 at step 415, in some embodiments, with these pickup details. The method ends after step 415.

Modifications, additions, or omissions may be made to the methods described herein without departing from the scope of the disclosure. For example, the steps may be combined, modified, or deleted where appropriate, and additional steps may be added. Step 411 may be omitted and steps 409 and 413 may be combined such that a user may be notified at step 415 regarding both an indication that the prescription has been filled and the pickup details. As another example, a step 402 may be added for interoperability module 140 to transmit the prescription received at step 401 to pharmacy module 130. Additionally, the steps may be performed in any suitable order without departing from the scope of the present disclosure. While discussed as interoperability module 140 performing the steps, any suitable component of system 100 may perform one or more steps of the method.

Figure 5A:
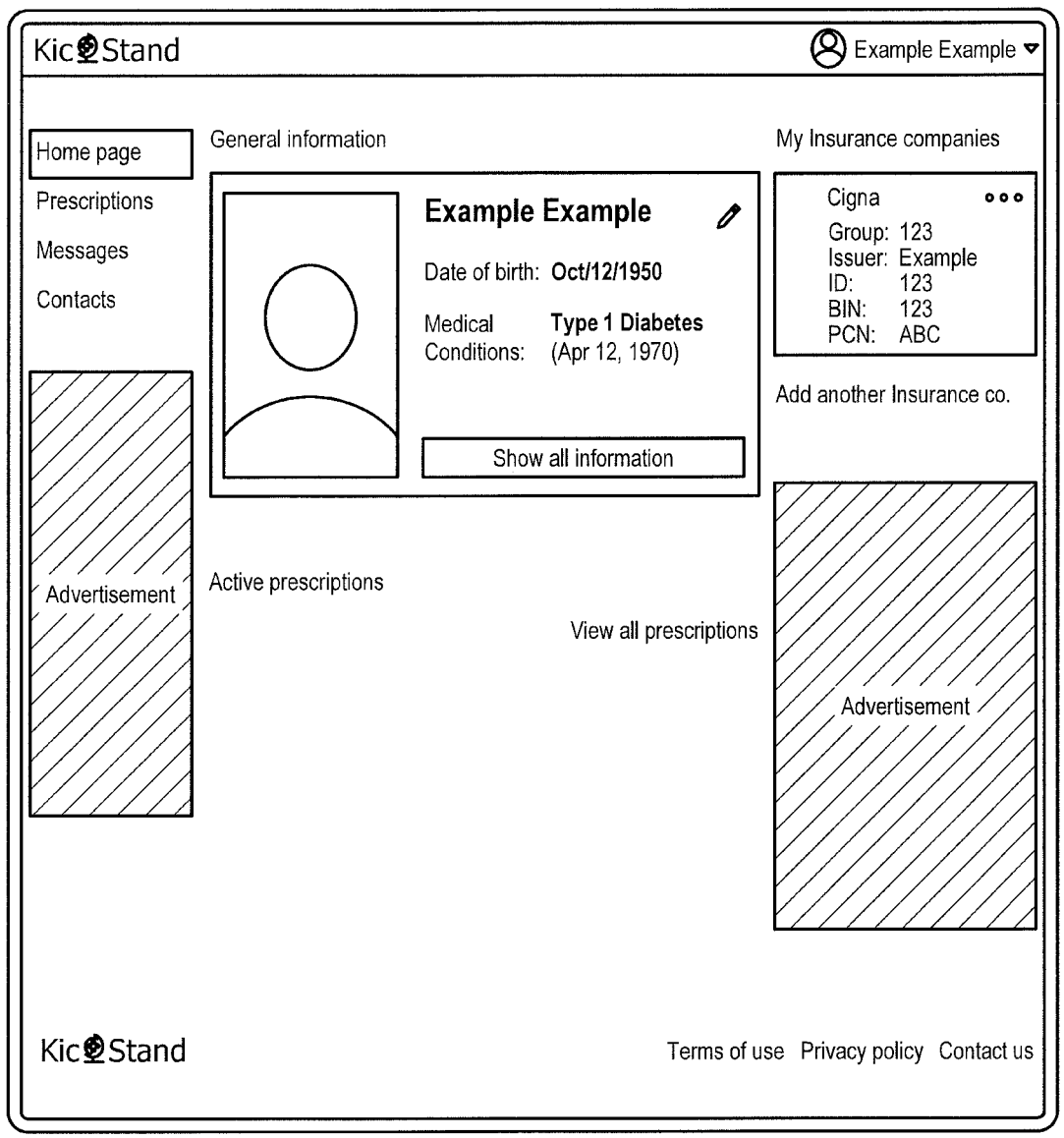
Figure 5B:
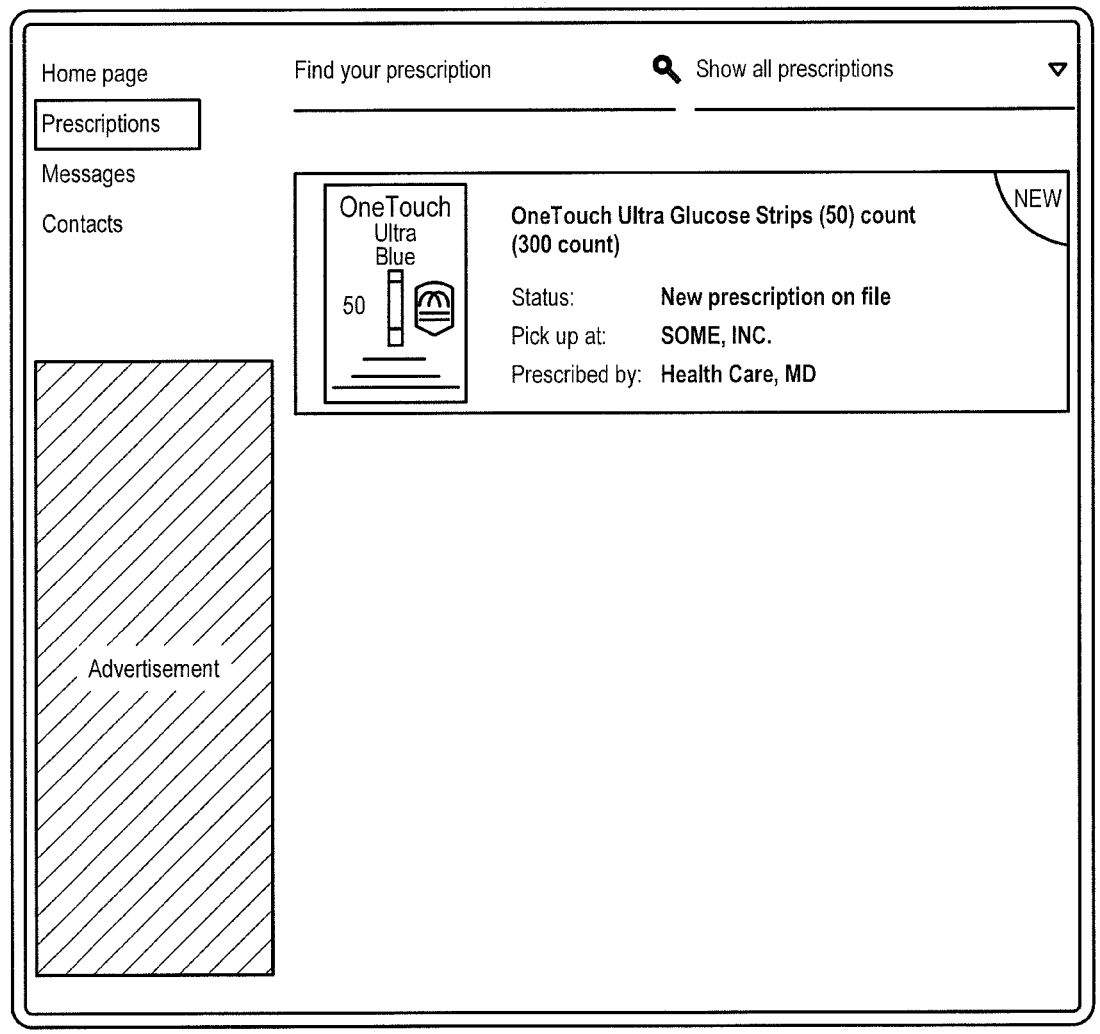

FIGS. 5A-C illustrates example user profiles that may facilitate interoperability among health care modules. The user profiles may be created using the process outlined in method 200 of FIG. 2 and created and/or utilized by interoperability module 140 of FIG. 1. FIG. 5A illustrates an example home page of a user profile (e.g., a patient). The home page may indicate general information associated with a user (e.g., name, date of birth, and medical conditions), list insurance companies associated with the user, and include options for more information about the patient ("show all information," "view all prescriptions," etc.). In some embodiments, the user profile may group together related pieces of information. For example, the user profile may show a medical condition of the patient, as well as related prescription information such as the drugs and/or medical devices the patient uses to treat that medical condition. The user profile may also show codes related to the medical condition and prescriptions, such as CPT codes for the medical condition, NDC and HCPCS codes for any prescriptions of medicine or medical devices. By grouping together information, the user profile efficiently stores the medical information for the user and can quickly identify the medications and/or medical devices used by the patient, and for which medical diagnosis each is related to. The user profile may contain any information that facilitates interoperability among health care modules, and thus FIG. 5A should not be construed as a limiting example of what may be included.

FIG. 5B illustrates a prescription tab available on the user profile. The prescription tab may show any number of prescriptions, as well as sorting the prescriptions by age, frequency, importance, or any other factor. In some embodiments, prescriptions may also be searched. In some embodiments, a prescription may be selected such that more information about the prescription is displayed. The prescription tab may contain any information related to relevant prescriptions and thus FIG. 5B should not be construed as a limiting example of what may be included.

FIG. 5C illustrates a prescription page that includes more detailed information about a particular prescription. For example, the prescription page may show the associated health care professional that prescribed the prescription, any alternatives, date created, dosage and directions, quantity, and any other information related to the prescription. The prescription page may further include insurance information, such as the company, whether the prescription is covered, copay and deductible information, and any other related information. The prescription page may further provide an option to start a chat or message with a fulfillment center or health care professional so that the patient may ask any questions. The prescription page may contain any information related to relevant prescriptions and thus FIG. 5C should not be construed as a limiting example of what may be included.

FIG. 6 illustrates an example interface for creating a new prescription and facilitating interoperability between health care professional modules, patient modules, and pharmacy and/or DME provider modules. The new prescriptions may be created using the process outlined in method 300 of FIG. 3 and created and/or utilized by interoperability module 140 of FIG. 1. FIG. 6 illustrates an interface that a health care professional may view when entering a new prescription for a patient (e.g., "Example Example"). When interoperability module 140 receives the prescription name and amount, it may automatically determine whether the prescription is covered by the patient's insurance. FIG. 6 illustrates an example where the insurance does not cover the prescription, displaying the insurance information and an indicator that the prescription is not covered (e.g., highlighted text and/or a "no" symbol). Interoperability module 140 may further identify an alternative prescription (e.g., "Atovastatin") and display an option for the health care professional to "use this product." Because interoperability module 140 is able to automatically determine coverage, a health care professional may be notified before providing the prescription to patient and/or transmitting the prescription to a fulfillment company. The interface of health care professional module 120 may contain any information related to users and/or relevant prescriptions and thus FIG. 6 should not be construed as a limiting example of what may be included. Technical advantages of particular embodiments of the present disclosure include reconfiguring an existing data structure to create a new data structure to allow health care modules to communicate health care information between disparate components. This improvement alleviates compatibility concerns between different systems components, thereby creating increased flexibility in exchanging electronic records. Additionally, a system may be configured to analyze data in an electronic record and extract a portion of data from the electronic record, thereby conserving the computational resources and bandwidth consumed by unnecessarily extracting all the data, some of which may be irrelevant.

In an embodiment, a system is configured to create a first user profile and associate the first user profile with other user profiles, thereby conserving the computational resources and bandwidth consumed by adding additional information contained in other user profiles to the first user profile.

In an embodiment, a system is configured to create a second electronic record that is compatible with more than one health care module, thereby conserving the computational resources and bandwidth consumed by creating and maintaining duplicate electronic records, each in a different format unique to each health care module.

Other technical advantages of the present disclosure will be readily apparent to one skilled in the art from the following figures, descriptions, and claims. Moreover, while specific advantages have been enumerated above, various embodiments may include all, some, or none of the enumerated advantages.

Although the present disclosure has been described with several embodiments, a myriad of changes, variations, alterations, transformations, and modifications may be suggested to one skilled in the art, and it is intended that the present disclosure encompass such changes, variations, alterations, transformations, and modifications as fall within the scope of the appended claims.

What is claimed is:

1. A system, comprising:
a memory configured to store code configured for extracting data from electronic records and creating additional electronic records in a desired data structure that is different from an initial data structure;
an interface communicatively coupled with the memory, and configured to:
receive a first electronic record of a patient, the first electronic record having a first data structure;
receive a second electronic record from a first computing device associated with an insurance organization, the second electronic record comprising information regarding medical coverage, the second electronic record having a second data structure, wherein the second data structure is incompatible with a second computing device associated with a patient;
a processor communicatively coupled to the memory and the interface, the processor configured to:
extract, by at least executing the code, data relating to a medical service from the first electronic record;
extract, by at least executing the code, data relating to medical coverage for the patient from the second electronic record;
based at least on the extracted data from the first and the second electronic records, create, by at least executing the code, a third electronic record comprising data relating to the medical service and data relating to the medical coverage, the third electronic record having a third data structure that is compatible with the second computing device, wherein the third data structure is different from each of the first and second data structures; and
based on the third electronic record, determine whether the medical service is covered for the patient.

2. The system of claim 1, the processor further configured to determine a current procedural terminology (CPT) code related to the medical service.

3. The system of claim 1, the processor further configured to:
based on the third electronic record, determine that the medical service is covered for the patient; and
determine a cost for the patient.

4. The system of claim 1, the processor further configured to:
based on the third electronic record, determine that the medical service is not covered for the patient; and
determine a cost for the patient.

5. The system of claim 1, wherein the medical service is related to a dental or vision service.

6. The system of claim 1, the processor further configured to:
create a profile of the patient based in part on the first electronic record of the patient; and
cause to display the profile to a health care professional related to the medical service.

7. The system of claim 1, the processor further configured to:
receive an indication relating to a medical condition of the patient; and
add the medical condition to a profile of the patient.

8. A non-transitory computer-readable medium encoded with logic, the logic, when executed by a processor, operable to:
store code configured for extracting data from electronic records and creating additional electronic records in a desired data structure that is different from an initial data structure;
receive a first electronic record of a patient, the first electronic record having a first data structure;
receive a second electronic record from a first computing device associated with an insurance organization, the second electronic record comprising information regarding medical coverage, the second electronic record having a second data structure, wherein the second data structure is incompatible with a second computing device associated with a patient;
extract, by at least executing the code, data relating to a medical service from the first electronic record;
extract, by at least executing the code, data relating to medical coverage for the patient from the second electronic record;
based at least on the extracted data from the first and the second electronic records, create, by at least executing the code, a third electronic record comprising data relating to the medical service and data relating to the medical coverage, the third electronic record having a third data structure that is compatible with the second computing device, wherein the third data structure is different from each of the first and second data structures; and
based on the third electronic record, determine whether the medical service is covered for the patient.

9. The computer-readable medium of claim 8, wherein the logic is further operable to determine a current procedural terminology (CPT) code related to the medical service.

10. The computer-readable medium of claim 8, wherein the logic is further operable to:
- based on the third electronic record, determine that the medical service is covered for the patient; and
- determine a cost for the patient.

11. The computer-readable medium of claim 8, wherein the logic is further operable to:
- based on the third electronic record, determine that the medical service is not covered for the patient; and
- determine a cost for the patient.

12. The computer-readable medium of claim 8, wherein the medical service is related to a dental or vision service.

13. The computer-readable medium of claim 8, wherein the logic is further operable to:
- create a profile of the patient based in part on the first electronic record of the patient; and
- display the profile to a health care professional related to the medical service.

14. The computer-readable medium of claim 8, wherein the logic is further operable to:
- receive an indication relating to a medical condition of the patient; and
- add the medical condition to a profile of the patient.

15. A method comprising:
- storing code configured for extracting data from electronic records and creating additional electronic records in a desired data structure that is different from an initial data structure;
- receiving, by an interface, a first electronic record of a patient, the first electronic record having a first data structure;
- receiving, by the interface, a second electronic record from a first computing device associated with an insurance organization, the second electronic record comprising information regarding medical coverage, the second electronic record having a second data structure, wherein the second data structure is incompatible with a second computing device associated with a patient;
- extracting, by a processor executing the code, data relating to a medical service from the first electronic record;
- extracting, by the processor executing the code, data relating to medical coverage for the patient from the second electronic record;
- based at least on the extracted data from the first and the second electronic records, creating, by the processor executing the code, a third electronic record comprising data relating to the medical service and data relating to the medical coverage, the third electronic record having a third data structure that is compatible with the second computing device, wherein the third data structure is different from each of the first and second data structures; and
- based on the third electronic record, determining, by the processor, whether the medical service is covered for the patient.

16. The method of claim 15, further comprising determining, by the processor, a current procedural terminology (CPT) code related to the medical service.

17. The method of claim 15, further comprising:
- based on the third electronic record, determining, by the processor, that the medical service is covered for the patient; and
- determining, by the processor, a cost for the patient.

18. The method of claim 15, further comprising:
- based on the third electronic record, determining, by the processor, that the medical service is not covered for the patient; and
- determining, by the processor, a cost for the patient.

19. The method of claim 15, further comprising:
- creating, by the processor, a profile of the patient based in part on the first electronic record of the patient; and
- displaying, by the interface, the profile to a health care professional related to the medical service.

20. The method of claim 15, further comprising:
- receiving, by the interface, an indication relating to a medical condition of the patient; and
- adding, by the processor, the medical condition to a profile of the patient.

* * * * *